United States Patent [19]

Schapira et al.

[11] 4,125,575

[45] Nov. 14, 1978

[54] PHOSPHONYLATED AMIDES

[75] Inventors: Joseph Schapira, Paris; Jacques Ruel, Saint-Gratien; Alain Bleriot, Tremblay les Gonesses, all of France

[73] Assignee: Compagnie Francaise de Produits Industriels, Gennevilliers, France

[21] Appl. No.: 706,261

[22] Filed: Jul. 19, 1976

[30] Foreign Application Priority Data

Jul. 18, 1975 [FR] France .................................. 75 22578

[51] Int. Cl.$^2$ .............................................. C07F 9/40
[52] U.S. Cl. ..................................... 260/923; 260/932; 260/938; 260/942; 260/943; 427/390 D
[58] Field of Search ............... 260/923, 938, 942, 943, 260/932, 984

[56] References Cited

U.S. PATENT DOCUMENTS

| | | | |
|---|---|---|---|
| 3,381,062 | 4/1968 | Zahir | 260/943 X |
| 3,518,327 | 6/1970 | Fearing | 260/984 X |
| 3,579,532 | 5/1971 | Nachbur et al. | 260/943 X |
| 3,658,952 | 4/1972 | Nachbur et al. | 260/932 |
| 3,671,611 | 6/1972 | Nachbur et al. | 260/932 |
| 3,691,277 | 9/1972 | Stolzer et al. | 260/984 X |
| 3,742,095 | 6/1973 | Walsh | 260/943 |
| 3,808,292 | 4/1974 | Petersen et al. | 260/932 |
| 3,809,730 | 5/1974 | Polevy et al. | 260/943 X |
| 3,937,612 | 2/1976 | Schwarzer et al. | 260/938 X |

*Primary Examiner*—Richard L. Raymond
*Attorney, Agent, or Firm*—Larson, Taylor and Hinds

[57] ABSTRACT

The invention concerns new phosphonylated amides.

12 Claims, No Drawings

PHOSPHONYLATED AMIDES

These amides correspond to the general formula

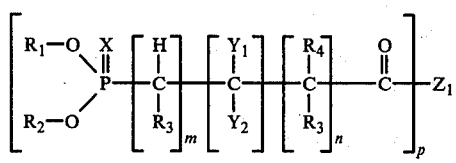

in which X is oxygen or sulphur, $Y_1$, $Y_2$ represent hydrogen or an alkyl or alkene group in $C_1$–$C_4$; $R_1$, $R_2$, $R_3$, $R_4$, $R_5$ represent an alkyl, alkene or alkyl halide group; $R_3$, $R_4$, $R_5$ can be in addition a hydrogen (atom); $Z_1$, $Z_2$ are residues containing more than one atom of nitrogen corresponding to guanidine, an alkylguanidine, an alkyl urea, alkenepolyamines, aminoguanidine or hydrazine; $m$ and $n$ are 0 or 1 and $p$ is 1 or 2.

These phosphonylated amides are used especially as flameproofing agents.

The invention has as its object new compounds of the phosphonylated and thiophosphonylated amide type, depending on circumstances, methylolated or alcoxymethylated.

The invention also has as its object a preparation process of the new compounds as well as their application as flameproofing agents especially for cellulose fibres.

Compounds of the type in question which are already known have been used to flameproof cotton fabrics but necessitated — in order to make it so that the fixing of these compounds on to the cellulose fibres was sufficiently strong to resist washing or cleaning operations — using them in conjunction with important quantities of amino plastics especially the N-hydroxymethylated or N-alcoxymethylated derivatives of amino-s-triazine, these gave to the treated fabric a rough, disagreeable hand and acted unfavourably on its physical properties.

An object of the invention moreover is to put at the disposal of the user flameproofing agents which do not present this difficulty and which are adapted to be fixed on to fibre either directly or by using a small proportion of amino plastic.

The compound of the invention has the general formula:

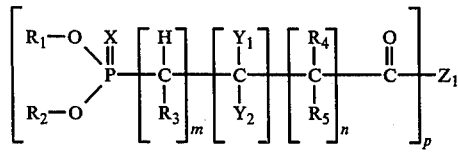 (I)

in which

X represents an atom of oxygen or an atom of sulphur $Y_1$ and $Y_2$ represent independantly of one another either an atom of hydrogen or an alkyl or alkene radical with 1 to 4 atoms of carbon and, depending on circumstances, having at the end of the chain an amide group with the formula

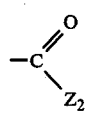

$R_1$, $R_2$, $R_3$, $R_4$, $R_5$ represent an alkyl, alkyl halide or alkene radical having 1 to 4 atoms of carbon, the substituents $R_3$, $R_4$ and $R_5$ being able, in addition, to represent an atom of hydrogen.

$Z_1$ and $Z_2$ represent a residue of a compound containing more than one atom of nitrogen chosen from the group made up of guanidine, alkylguanidines, alkyl ureas, ethylenediamine, diethylenetriamine, triethylenetetramine, aminoguanidine and hydrazine and its derivatives, it being understood that the amine functions of these residues can be methylolated or alcoxymethylated.

$m$ and $n$ represent independantly of one another the number 0 or 1

$p$ represents the number 1 or 2 except when $Z_1$ is guanidine or alkylguanidine or an alkyl urea in which case $p = 1$ Of the compounds shown in formula (I) the most particularly preferred are those which correspond to the following formulae:

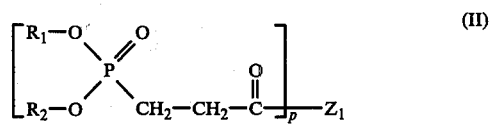 (II)

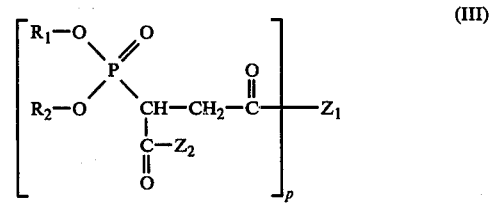 (III)

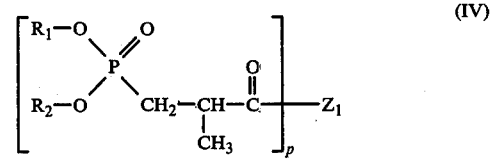 (IV)

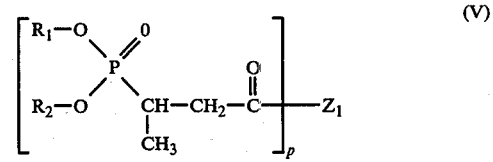 (V)

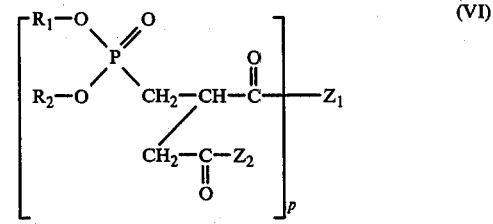 (VI)

in which $R_1$, $R_2$, $Z_1$, $Z_2$ and $p$ have the above-indicated significations.

Other preferred groups of compounds corresponding to the general formula (I) are those which are shown by the following partial formulae:

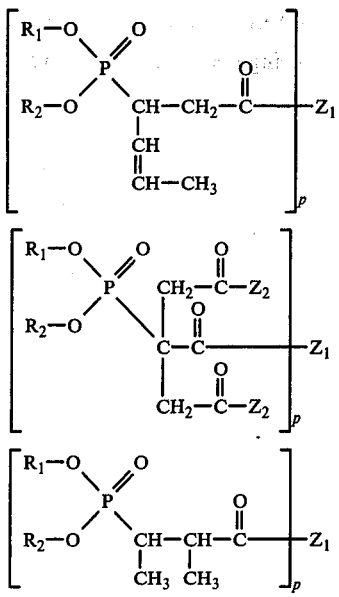

in which $R_1$, $R_2$, $Z_1$, $Z_2$ and $p$ have the significations given above.

The most particularly preferred compounds are of formulae (II) to (VI) in which $R_1$ and $R_2$ are methyl, ethyl, propyl, chloroethyl, dichloropropyl radicals and $Z_1$ and $Z_2$ are residues of guanidine, ethylenediamine, hydrazine.

The preparation process of the compounds according to the invention is characterised in that a compound containing more than one atom of nitrogen of the group comprising guanidine, alkylguanidines, alkyl ureas, ethylenediamine, diethylenetriamine, triethylenetetramine, aminoguanidine and hydrazine and its derivatives, depending on circumstances in excess, are made to react with a phosphonocarboxylic ester of the general formula:

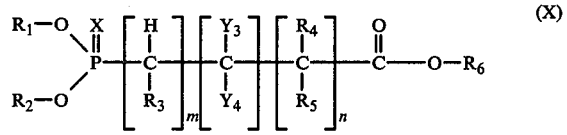

in which $R_1$, $R_2$, $R_3$, $R_4$, $R_5$, and $m$ and $n$ have the significations given above.

$Y_3$ and $Y_4$ represent either a hydrogen atom or an alkyl or alkene radical comprising 1 to 4 carbon atoms and having, depending on circumstances, at the end of the chain an ester group with the formula:

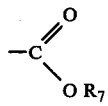

$R_6$ and $R_7$ represent either lower aliphatic residues with 1 to 4 carbon atoms or aromatic residues such as the phenyl group.

The preparation of esters with the formula (X) is known. In particular it is the object of British patent specifications No. 693,742 and 695,782. This preparation consists in the addition of dialkyl phosphite to unsaturated aliphatic esters in the presence of an alkaline catalyst of the alcoholate or alkaline metallic amide type.

The reaction of esters with the general formula (X) with compounds containing more than one atom of nitrogen is advantageously performed in an aqueous or hydro-alcoholic medium or in an organic solvent according to the chosen amine. One performs the reaction preferably in a medium made up of a mono- or polyalcohol, depending on circumstances, partially etherified or in an ether such as dioxane.

With ethylenediamine and hydrazine one can perform the reaction in an aqueous or solvent medium, either anhydrous or not. With guanidine one works in an anhydrous solvent such as methanol, ethanol, n- and iso-propanol, the presence of water assists the formation of carboxylated amine; so that the water content in the solvent remains relatively low, e.g. less than 10%, the properties of the flameproofing product obtained are not altered.

The temperature of the reaction between the ester of the formula (X) and the compound containing more than one atom of nitrogen depends on the chosen amine, generally it is between 1° and 120° C. and preferably between 60°-100° C. Advantageously one works at the boiling point of the solvent and operates under reflux.

When one uses guanidine one operates at a temperature between 0°-30° C. preferably at a temperature close to 10° C. and one slowly introduces the guanidine solution into the ester in order to avoid over-heating. The guanidine is, in fact, unstable when heated and decomposes to give rise particularly to compounds of urea.

It can be advantageous moreover if the reaction takes place within an anhydrous solvent to use a catalyst of the metallic amide, alkaline methylate, alkaline earth or magnesium methylate types.

The length of the reaction is from 3 to 72 hours according to whether one works from cold or from hot. From hot the length is 6–12 hours, from cold it is from 8–72 hours.

In order to achieve this reaction one will use a sufficient quantity of amine which will advantageously comprise between about ½ mole and 3 moles of amine for each mole of ester, preferably nearly one mole of amine per mole of ester. In certain particular cases, especially with guanidine, it is better to have a large excess of amine.

One can use less than a mole of amine for each ester function and in this case 2 molecules of ester can react with a single molecule of amine.

At the end of the reaction certain amides precipitate, in particular when the reaction takes place in an anhydrous solvent. They are then filtered and dried. If the amide does not precipitate, in particular when the amides are prepared in an aqueous or hydro-alcoholic medium, and even in certain cases when one works with an anhydrous solvent, the reaction medium is concentrated, depending on circumstances, under vacuum until the final product is obtained.

Certain of the compounds containing more than one atom of nitrogen mentioned above, particularly guanidine and aminoguanidine, are not stable in a free state but only in the salt state, in this case, in order to bring about the reaction described above, one can prepare the free amine starting from one of its salts by dissolving the amine salt in alcohol and by treating the solution with a stoichiometric quantity or alkaline or alkaline earth alcoholate; the alkaline or alkaline earth salt of the anion precipitates then and is eliminated by filtration, the amine is recovered in solution.

One can precipitate the anion in an anhydrous medium and, in this case, obtain an anhydrous amine in a solvent. In the place of alkaline or alkaline earth alcoholate one could use a strong base partially soluble in alcohol as, for example, potash or soda, in this case one obtains a solution containing slight quantities of water originating from the reaction of the base and the acid which was fixed to the amine.

This water, in case of necessity, can be eliminated by reaction with a stoichiometric quantity of calcium carbide and filtration of the precipitate obtained either by addition of a suitable quantity of soda or potash so as to obtain a concentrated soda washing which one decants by leaving a dehydrated amine solution remaining floating above.

The water can also be eliminated by the addition of quicklime which is changed into slaked lime and is eliminated by filtration.

For certain compounds containing more than one atom of nitrogen which are only stable in the form of salts one can make the ester with formula (X) and the salt react directly in the water or in the alcohol.

For that, one introduces into the ester, the amine salt and the stoichiometric quantity of soda or potash in relation to the amine salt, one leaves the reaction to work itself out. Then one filters the salt formed by the anion of the amine salt and sodium or potassium and one obtains an amide according to the invention in solution in water.

The compounds according to the invention can also be prepared by means of a second process. This second process is characterised in that one can make a mono- or polycarboxylic ester containing either one or several double bonds but without the phosphonic grouping react with one of the compounds containing more than one atom of nitrogen in the group mentioned above under the conditions described above which leads to the corresponding amide which one makes react in its turn, after drying, with the appropriate dialkyl phosphite in the presence of a catalyst, for example alkaline alcoholate or alkaline earth, a metallic amide or an alkaline hydride, sodium naphthalene or amines of the triethyleneamine type in an alcohol solution.

In order to achieve the addition of dialkyl phosphite one can work in the following manner. One disperses, under agitation, the unsaturated carboxylic amide obtained into the dialkyl phosphite, depending on circumstances, in excess and one introduces the catalyst in small quantities because the reaction is exothermic until one observes a rise in temperature, the product is then maintained at 50°–60° C. for several hours in order to complete the reaction.

The phosphonylated amide can be recovered if it is soluble in the dialkyl phosphite in excess by driving off the excess dialkyl phosphite by distillation under vacuum; if it is not soluble it is filtered and dried.

A third preparation process for compounds with the general formula (I) consists of submitting esters with the formula (X) to the action of phosphorus pentachloride when heated in sufficient quantity to form acid chlorides with carboxylic functions. One eliminates phosphorus oxychloride and the alkyl chloride formed by distillation, depending on circumstances the phosphono-carboxylic acid chloride can also be distilled if it is sufficiently stable. One can immediately make the chloride react on the chosen compound containing more than one atom of nitrogen either in the solid state or in an ether solution. The compound according to the invention precipitates to give a good yield.

The compounds according to the invention make up excellent flameproofing agents not only with respect to cellulose fibres and especially cotton, hemp, jute, linen and sisal but also with respect to textile fibres such as wool, silk or rayon. They are equally active with regard to wood or paper.

Flameproofing is obtained by fixing or incorporating respectively on or in these substrata phosphonylated amide compounds according to the invention.

Fixing can be achieved by direct action of the compound according to the invention on the substratum, particularly the chosen material, the said compound being then, as a preliminary, methylolated or alcoxymethylated in order to make the direct fixing possible. This is particularly the case with compounds according to the invention which are obtained with guanidine or ethylenediamine which have sufficient reactivity to react directly after methylolation or alcoxymethylation.

Fixing can also be achieved by using a small quantity of amino plastic particularly derivatives of amino-s-triazine (having undergone N-hydroxymethylation or N-alcoxymethylation) in conjunction with compounds according to the invention which then do not need to be preliminarily methylolated or alcoxymethylated. In any case, this second method of fixing permits a particularly strong bond of the compound according to the invention, making the flameproofing particularly resistant to various drycleaning and washing processes.

In order to methylolate those amides according to the invention which are stable under heat, the amide is advantageously dissolved in a solution of formaldehyde or it is mixed with paraformaldehyde or any other compound or mixture able to produce formol in a stoichiometric quantity or in excess, at a temperature varying from 50° to 150° C., depending on circumstances in the presence of basic catalysts. The latter can be strong bases such as soda, potash, basic salts such as sodium carbonate, or oxides such as magnesium oxide.

On heating, a very viscous mass is formed which softens in time. It is then recovered with small quantities of pure water a water-alchol mixture and, depending on circumstances, one filters the precipitate formed made up of the methylolated derivative.

For unstable amides or those with too high a melting point, one can proceed to methylolation by dissolving the amide in formaldehyde at 30% or at 37% in water then, on heating the solution for 3 to 12 hours at temperatures from 30° to 70° C., the pH being maintained at a value between 7.5 and 11 inclusive by the addition of sodium carbonate or of strong bases. The solution is then cooled, the pH is brought back to between 4 and 5 and the solution is concentrated if necessary.

In order to alcoxymethylate the amides according to the invention, one can make the methylolated product react on an alcohol. In order to do this the methylolated product is dissolved in an excess of alcohol, chosen preferably from among the methyl, ethyl, isopropyl, n-propyl or butyl alcohols, then the solution obtained is acidified with hydrochloric acid, either gaseous or in solution, in order to bring the pH to a value between 1 and 5 inclusive. The reaction mixture is maintained at a temperature between 50° and 70° C. inclusive for 1 to 5 hours, then it is neutralised to a pH between 6 and 8 inclusive and cooled.

Flameproofing treatments of fabrics can be effected after dying and can be associated with treatments aimed at, for example, waterproofing or to crease-resistance.

In order to effect flameproofing treatment on fabric resistant to drycleaning and not altering the qualities of the treated materials, one can advantageously use an aqueous bath containing at least a compound with the formula (I) and, as necessary, adjuvants usually used in treating textile materials. The fabric is impregnated in the treatment bath according to traditional methods and particularly by padding the fabric in the bath, squeezing and drying. The latter is effected preferably at a temperature going from 50° to 120° C. The treatment bath for flameproofing which is strong enough to be drycleaned is advantageously made up of:

5 to 50% phosphonylated amide (I) not methylolated, neutralised at pH 7 by means of an acid, for example phosphoric acid, nitric acid, sulphuric acid, hydrochloric acid, acetic acid or propionic acid.

depending on circumstances 0.05 to 0.1% of a surfactant agent depending on circumstances other finishes normally used in textile treatments.

In order to obtain a strong flameproofing treatment expecially of cellulose fabrics, not only resistant to drycleaning but also to household washing, one will use preferably compounds with formula (I) in which the amide groupings are derivatives of guanidine or ethylenediamine in conjunction with an amino-s-triazine derivative; one obtains thus a very good result in fixing the compound onto the fabric which makes it possible to utilise small quantities of the products and consequently the fabric properties are only slightly modified. Then the fabric to be flameproofed is impregnated in an aqueous bath containing advantageously:

at least one product with the formula (I) the amide groupings of which are derived from guanidine or ethylenediamine preferably, at least one amino-s-triazine derivative at least partially N-hydroxymethylated or N-alcoxymethylated depending on circumstances at least one hydroxymethylated or alcoxymethylated derivative of urea, of ethylene urea or of compounds including urea, at least one acid compound or a compound giving acid products in water and intended to control the pH of the bath at values between 0.5 and 5 inclusive and preferably between 2.5 and 4.5.

depending on circumstances a compound with a latent acidity intended to improve the hardening of amino-s-triazine derivatives.

It is equally possible to add to the treatment bath different adjuvants as, for example a surfactant agent, in order to improve the wetting power of the bath to a concentration of the order of 0.05 to 1%. One can also introduce softening agents as, for example, amides of fatty acids or an aqueous emulsion of a polyethylene resin in small quantity and less than about 20 g/l.

The quantity of phosphonylated amide compound in the baths is such that the phosphorus content of the bath is of the order of 0.5 to 7% and, preferably, of 1 to 4%. The content chosen depends on wet pick up and on degree of flameproofness required.

One utilises advantageously as in the case of amino-s-triazine derivatives of ammeline, ammelide, guanamine or especially of melamine. Preferably one utilises the tri-, tetra-, penta- and hexa-hydroxymethylmelamines, partially or totally etherified. Preferably the derivatives of the amino-s-triazines are used at the rate of 20 to 200g per liter of treatment bath.

As for the acid compound to control the pH of the bath one can use strong mineral acids or its chloride as, for example, hydrochloric acid, sulphuric acid, phosphoric acid, phosphorus trichloride, phosphorus pentachloride or phosphorus oxychloride.

Finally as for the compound with latent acidity one can use, for example, ammonium chloride, an amine hydrochlorate, an acid phosphate of ammonium or amine, zinc nitrate, magnesium chloride, depending on circumstances joined to acids such as formic, acetic, propionic, citric, lactic.

The acid compounds and those with latent acidity are introduced into the bath at the rate of 5 to 50 g/l.

The treatment of textiles is done preferably by immersion from cold in the bath. The impregnated textile is then squeezed and partially or totally dried, preferably at high temperatures.

In order to give the treated fabrics a strong flameproofing resistance to washing, the fixing is completed by treatment at a high temperature, of the order of 100° to 185° C., preferably 120° to 170° C., for a period of time between 1 and 20 minutes inclusive. Longer times and higher temperatures favour the fixing process but can damage the physical qualities of the fabric (just as can too strong an acidity or too great a quantity or compound with latent acidity).

The fabric is then washed in a hot, dilute alkaline solution in order to eliminate surplus products of the bath which have not been fixed onto the fabric. In order to finish the treatment the fabric or the fibre is rinsed several times then spun and dried.

The following examples illustrate particular methods of application of the invention.

In the examples the flameproofness is measured according to the standard DIN 53 906 and the limit oxygen index is measured according to the standard ASTMD 2 863/70.

The invention equally concerns materials and especially textile materials treated by means of one of the phosphonylated amide compounds, or by one of the processes described above.

EXAMPLE 1

Diethyl diethyl-phosphonosuccinate is prepared as described in British Pat. No. 695,782 starting with diethyl phosphite and diethyl maleate.

One obtains a yield of 87% after distillation at 116°–118° C. under 0.07 mm of mercury of a product ot 98% purity appreciated by determination.

In a 100 cc four necked flask fitted with an agitator, a thermometer, a reflux condenser and a funnel. One puts 20g (0.0645 mole) of diethyl diethyl-phosphonosuccinate.

One heats to 110°–115° C. with the aid of an oil bath in which this temperature is maintained throughout the entire reaction, one then pours slowly 7.75g (0.129 mole) of ethylenediamine over a period of about two hours. One observes a slight reflux which steadily increases whilst the temperature in the flask decreases to reach 90°–95° C. four hours later.

One then distills, under a partial vacuum, the ethylenediamine which has not reacted and the ethanol formed. One obtains a wax which one recovers by 40g of water which is then driven off under reduced pressure to take out the last traces of ethylenediamine which have not reacted. One then dries the product in a drying chamber under vacuum and obtains 21g of a yellow, friable, hygroscopic solid the nitrogen content of which is 14.5% (theory: 16.6%) and which is 85% 2-diethylphosphonosuccinyl bis (ethylenediamine)

The 21g of 2-diethylphosphonosuccinyl bis (ethylenediamine) is dissolved in 23.70g of 30% formol and the pH of the solution is brought to between 8 and 9. One heats for 2 hours in a bain marie adding soda to maintain the pH between 8 and 9. Then one cools and obtains 48 g of solution.

By titration of the free formol, methylolation takes place to 65%.

One obtains a clear yellow syrup containing 3.50% phosphorus. One adds to it 3g of a highly etherified hexamethylol-melamine, one controls the pH of the whole at 3 with phosphoric acid and one impregnates a cotton fabric of 180 g/m². The fabric is then dried until it has a residual humidity of 15% and then placed in a ventilated drier for 20 minutes at 165° C.

The fabric is washed at 60° C. for 5 minutes in a solution containing 5 g/l of sodium carbonate, then dried.

The weight add-on is 17% in relation to the fabric. After three washings of 15 minutes at 60° C. the fabric is still flame-resistant, satisfying the standard DIN 53906.

EXAMPLE 2

In a four necked flask fitted with an agitator, a thermometer, reflux condenser and dropping funnel, one puts 25.8g (0.0832 mole) of diethyl diethyl-phosphonosuccinate which one raises to 100°–105° C. Then one introduces slowly through the dropping funnel 5g (0.0833 mole) of 98% ethylenediamine still maintaining the temperature by means of an oil bath. One leaves the reaction to proceed for 4 hours when a slight reflux is established, the temperature in the flask being in the region of 95°–98° C.

One obtains a viscous product which one recovers with ethanol, then three times with water which one drives off each time under reduced pressure. The distillate is then neutral. One concentrates it under vacuum and then one dries it in the ventilated drier at 60° C., then in a phosphorus pentoxide desiccator. One obtains 26.78g of diethylphosphonosuccinylethylenediamine, assaying 8.1% nitrogen (theory 10.1%).

A quantity of 14.3g of this amide is dissolved in 10.28g of 30% formol and one brings the pH up to 10 soda, one warms for 8 hours at 60° C. The mixture is then cooled and titrated. 7% of free formol remains which shows that one has methylolated at the rate of one methylol radical per mole of ethylenediamine.

One prepares a bath by adding 3g of a totally etherified methylolmelamine to the preceding solution and one brings the pH to 3 by phosphoric acid.

One impregnates a cotton fabric of 200g/m² with this solution one dries to a residual humidity of 20% and then one puts it in a ventilated drier for 20 minutes at 160° C. The fabric is then washed in carbonated water to eliminate the residues of acid, then dried. It has a weight increase of 14% and has good flame resistance according to the standard DIN 53906.

EXAMPLE 3

One prepares 15g of 2-diethylphosphonosuccinyl bis (ethylendiamine), as in example 1, which one dissolves in 85g of water and which one neutralises to pH 7 with some drops of a strong acid.

One impregnates a fabric of 180g/m², one dries it at 60° C. and one tests it according to the norm DIN 53906.

The fabric has excellent stable flameproofnees after several dry cleanings.

EXAMPLE 4

One prepares methyl diethylphosphonopropionate as described in British Pat. No. 693,742, at 98% purity after distilling at 100° C. under 0.7 mm of mercury.

Into a 1000cc erlenmeyer flask one adds 14.7g of freshly cut sodium shavings in 300cc of absolute methanol sufficiently slowly to avoid any dangerous overheating. When everything is dissolved one pours the sodium methylate, over a period of about 1½ hours, in a dispersion of 66.7g of guanidine hydrochloride in 250cc of absolute methanol. One leaves the sodium chloride precipitation to proceeed for 1 hour, then one filters, one washes the cake with methanol and one recovers the anhydrous guanidine solution in methanol.

One recovers, by potentiometry and by a measure of nitrogen, 98% of the guanidine used.

Into a one liter, four necked flask fitted with an agitator, a thermometer, a reflux condenser and a dropping funnel fitted with calcium chloride guards, one puts 148g of methyl diethylphosphonopropionate and one cools with the aid of an external ice bath to 10° C.

One pours, under agitation, over a period of about 1½ hours the guanidine methanol solution whilst maintaining the temperature at less than 10° C. for 18 hours.

The solution is then concentrated in the cold under vacuum until an important precipitation is observed.

One filters and then recovers a precipitate which one washes with dioxan or a very small amount of anhydrous methanol.

One obtains, after drying, 138g of white crystallized product melting at 170°–172° C., the characteristics of which are as follows:

P: found 11.7%: N: found 16.7%. P: calculated 12.3%: N: calculated 16.7%.

Passing it over an acid resin shows that all the nitrogen is bonded in the form of carboxylic amide which is confirmed by an infra-red spectrum.

Into a 250cc three necked flask fitted with a mechanical agitator, a thermometer, a reflux condenser, one puts 57.4g diethylphosphonopropionyl guanidine, (0.228 mole) and 27.4g of polyoxymethylene (0.912 mole) and a small quantity of magnesium oxide. One melts the mixture and adds 28g of distilled water. One maintains the pH between 9 and 10 by adding sodium carbonate and one leaves it under agitation for 4 hours at 70° C.

One cools, eliminates the precipitate which is formed and measures the free formol, the weight of which is 9.32g, which corresponds to the formation of 2.6 functions methylol per mole of diethylphosphonopropionyl guanidine.

The phosphurus content in the solution obtained is 4.5%; the solution is then neutralised by 15.36g of 85% phosphoric acid.

Starting from this solution one prepares two baths: the first with the aid of 48.1g of the preceding solution to which one adds 0.77g of citric acid and 0.77g of magnesium chloride —6H₂O, and which one completes with 2.6g of water containing 0.05g of wetting agent based on polyethoxylated nonylphenol; the bath thus contains 3.7% of P due to diethylphosphonopropionyl guanidine.

the second with the aid of 50.66g of the preceding solution to which one adds 1.65g of citric acid and 1.65g of magnesium chloride-6H$_2$O, and which one makes up to volume by 56g of water containing 0.1g of wetting agent with a polyethoxylated nonylphenol base, the bath is then controlled to 1.80% of phosphorus due to the diethylphosphonopropionyl guanidine.

Into these two baths one pads two lengths of cotton fabric of 240g/m$^2$ and roll squeezes them. They are then dried to a residual humidity of 20%, then placed for 15 minutes in a ventilated drier at 170°-175° C. They are then washed for 5 minutes at 90° C. in a solution maintained at 20g/l of sodium carbonate, then rinsed and dried.

The weight percent of phosphorus bonded to the fabrics treated by the first and second baths are respectively 2.1 and 1.8% which is excellent.

Moreover, the fabrics have retained all their softness after treatment and have a "very good hand".

One submits the treated fabrics to ten 30 minute washes at 60° C. in an alkaline solution, one rinses them in acidulated water then in pure water and one tests them according to the standard DIN 53906. The postcombustion times are nil and the tear heights are less than 7cm.

After five further washes the fabric treated with the first bath still shows excellent flame resistance whilst that treated with the second bath burns. The weight percent of phosphorus on the fibre are then respectively 1.25% P and 1% P.

EXAMPLE 5

Into a 500cc erlenmeyer flask one introduces 200cc of 99.5% methanol and one disperses in it 39.0g of 98% guanidine hydrochloride. Then one adds progressively 16g of soda in pellets avoiding the mass heating. One leaves it under agitation for 2 hours, then one filters through a sintered filter and one rises the cake with 50cc of methanol.

The two alcohol phases are recovered. Into a 500cc four necked flask fitted with an agitator, a thermometer, a condenser and a dropping funnel one puts 59g of distilled dimethyl diethylphosphonomethylene- -succinate, and one pours, over a period of about 3 hours, through the dropping funnel, the guanidine methanol solution, whilst cooling exteriorly to avoid the temperature going higher than 10° C.

Then one leaves the whole in refrigeration for two days.

The contents of the flask is then concentrated under vacuum at an ambient temperature, until a very viscous wax is obtained which one leaves and which, in time, crystallises slowly.

The phosphorus content is 7%, which shows the presence of about 20% methanol.

The eluent of an aliquot part after passing over Dowex acid resin shows a certain acidity which is due to the presence of a chloride ion coming from the guanidine and to the formation of a part of guanidium carboxylate in the course of the reaction due to the presence of water coming from the action of the soda on the guanidine hydrochloride One prepares a bath containing 2.2% phosphorus in the phosphonate form by dissolving 31.5g of the preceding product in 30g of water, by acidifying to pH 4.3 by 6.5g of 85% phosphoric acid, by adding to it 6g of almost completely etherified methylol melamine and 1.5g of citric acid with 1.5g of magnesium chloride. The whole is made up to 100cc after adding a wetting agent of the polyethoxylated nonylphenol type.

One impregnates a cotton fabric of 280g/m$^2$ with the preceding bath, one squeezes it until a wet pick up of 120%, one dries it, then puts it in a ventilated drier for 20 minutes at 160°-165° C. The fabric is then washed for 5 minutes in carbonated water at 90° C., then rinsed and dried.

Then it has an oxygen index of 31%. Its index is still greater than 29% after 16 hours of washing at 60° C. in an alkaline medium.

EXAMPLE 6

One disperses under agitation 90g of guanidine carbonate in an erlenmeyer flask containing 200cc of methanol and one introduces gradually while keeping the temperature below 10° C. in an ice bath, 40g of soda pellets.

Then one leaves it to agitate for 2 hours at a temperature less than 10° C., then one filters, washes the sodium carbonate cake with 50cc supplementary of methanol and one gathers the methanolic fractions containing guanidine.

Into a 1 liter flask, one puts 238g of methyl diethylphosphono-3-methyl-2 propionate (obtained by adding diethyl phosphite to methyl methacrylate) and one pours through the funnel the guanidine methanolic solution whilst cooling outside with an ice bath. One leaves it agitating at a temperature lower than 10° C. for 2 hours, then one leaves it 48 hours under refrigeration.

The mixture is then slowly concentrated under vacuum at an ambient temperature. One obtains a slightly yellow viscous wax which assays 9.5% phosphorus.

One dissolves 22g of it in 50cc of water and one brings the pH to 4.3 by 3.4g of phosphoric acid, one adds 3.0g supplementary of 85% phosphoric acid and 5.5g of partially etherified methylolmelamine. One makes up to 100cc and one impregnates a cotton fabric of 280g/m$^2$, with a wet pick-up of 140° C. The fabric is dried then, raised for 15 minutes to 160°-165° C. Then it is washed at 90° C. in carbonated water and then rinsed. Finally it is dried.

The fabric thus treated has a limit oxygen index of 33% and its breaking strength is slightly modified.

After a 18 hours wash at 60° C. in an alkaline solution its limit oxygen index is still greater than 29% which is a good flameproofness.

EXAMPLE 7

One proceeds as in the preceding example but beginning with 238g of methyl-3-diethylphosphono-3-methyl propionate (obtained by adding diethyl phosphite to methyl crotonate).

One prepares a bath as in the preceding example, one impregnates in it a fabric of 280g/m$^2$, and one treats it as in example 6. The impregnated fabric shows as good flameproofing characteristics.

EXAMPLE 8

In a 500cc three necked flask fitted with an agitator, a reflux condenser and a thermometer, one introduces 112g of methyl diethylphosphonopropionate, 115g of methanol and 39.2g of ethylenediamine. The temperature of the mass rises to 35° C. and one then raises it to 60° C. for 12 hours. One leaves it to cool, then one concentrates under vacuum to drive off the methanol and ethylenediamine which have not reacted.

One contains 133g of a slightly yellow viscous oil which is diethylphosphonopropionyl ethylenediamine containing traces of methanol.

In a 250cc three necked flask fitted with an agitator, a thermometer and a reflux condenser containing 45g of the oil obtained, one introduces 8g of polyoxymethylene and one raises it to 70°-80° C. Then one adds 17g of water and one controls the pH to 8-9 by a small quantity of sodium carbonate.

One keeps it at 70° C. for 6 hours then cools.

One obtains 70g of a red solution containing 7.5% phosphorus.

One prepares a bath starting with 25g of this solution which one acidifies with 2.04g of 85% phosphoric acid and which one makes up to volume with 85g of water containing 1.9g of citric acid and 1.9g of magnesium chloride-6H$_2$O.

One then adds 7.5g of an almost completely etherified methylolmelamine and one homogenises it.

One impregnates a cotton fabric of 280g/m$^2$ in this solution then one dries it in the air and one places it for 1/4 hour in a ventilated drier at 165° C. The fabric is then washed in carbonated water, rinsed then dried.

One obtains a fabric the flame resistance of which, measured against the standard DIN 53906, resists several gentle washes at 40° C.

EXAMPLE 9

One makes up a bath with 24g of diethylphosphonopropionyl ethylenediamine, obtained in the preceding example, which one dissolves in 92g of water. Then one neutralises by adding 7.74g of phosphoric acid and one adds 3g of zinc nitrate and 8.5g of a partially etherified methylolmelamine.

One impregnates a cotton fabric of 280g/m$^2$ with a wet pick-up of 140%, one dries it and one puts it for ¼ hour at 160°-165° C. in a ventilated drier, then one washes it in carbonated water and rinses it.

One obtains a fabric which is still flame-resistant passing the standard 53906 after a three hours wash at 60° C. in the presence of sodium carbonate.

EXAMPLE 10

One makes up a bath with 15g of diethylphosphonopropionyl ethylenediamine and 82g of water. The whole is neutralised to pH7 by phosphoric acid and one impregnates a fabric of 280g/m$^2$ with it, roll squeezes and dries.

The weight add-on is slightly greater than 20%. The fabric is tested according to the standard DIN 53906. The tear length is less than 5cm and postcombustion is nil. The fabric keeps its flameproofing properties after several dry cleanings.

EXAMPLE 11

Into a 250cc erlenmeyer flask fitted with a mechanical agitator heated by a bain marie and surmounted with a condenser, one introduces 112g of methyl diethylphosphonopropionate, 30g of hydrazine hydrate and 30g of water. The whole is heated for 12 hours at 70°-80° C., then cooled and concentrated under vacuum. One obtains 114g of a white viscous oil the pH of which is less than 8.

One prepares a bath starting with 18g of this oil and 82g of water and one pads a fabric of 280g/m$^2$ in it. The wet pick-up is 100%.

The fabric is dried then tested. It shows excellent flame-resistance according to the standard DIN 53906 and is stable for several dry cleans.

EXAMPLE 12

Into a 500cc erlenmeyer flask with a magnetic agitator and cooled by an ice bath one introduces 135cc of 99.5% methanol and one disperses 61g of guanidine nitrate. One introduces then, on several occasions, over a period of one hour, 20g of soda in pellets. One leaves it to agitate 3 further hours whilst maintaining the temperature lower than 5° C. by ice. Then one filters the sodium nitrate precipitate formed, one washes it in 35cc of methanol and filters it again. One joins the methanolic phases and one collects 170 g of guanidine solution.

Into a 500cc three necked flask fitted with an agitator and a thermometer and containing 98 g of methyl dimethylphosphonopropionate one pours, over a period of one hour, the methanolic guanidine solution whilst maintaining the temperature at below 5° C. One agitates for two further hours then one leaves it for 48 hours under refrigeration. Then the solution is concentrated under vacuum at an ambient temperature and one obtains 128 g of a wax with 12% phosphorus which contains a little methanol and which is mainly dimethylphosphonopropionyl guanidine.

One sets up a bath with 2.2% phosphorus in the phosphonate form with 21 g of the product obtained which one dissolves in 79 g of water and one neutralises to pH 4 by 3.21 g of 85% phosphoric acid. One makes up this bath to volume with 1.7 g of citric acid, 1.7 g of magnesium chloride and 7g of a partially etherified methylolmelamine.

One impregnates a cotton fabric of 280 g/m$^2$ with the bath, with a wet pick-up of 130%, one dries it and puts it for ¼ hour at 165° C. Then it is washed for 5 minutes at 90° C. in water containing 5 g/l of sodium carbonate, rinsed then dried. The fabric has excellent flameproofing, according to the standard DIN 53906, and a limit oxygen index of 37%. After 17 hours of washing at 60° C. in water containing 2 g/l soap and 3 g/l sodium carbonate and after rinsing in water acidulated by hydrochloric acid, the fabric shows excellent flame resistance according to the standard DIN 53906 and has a limit oxygen index greater than 28%.

The fabric has a good hand and its physical properties are not greatly modified.

EXAMPLE 13

One proceeds as in the preceding example but with 112 g of methyl diethylphosphonopropionate and one obtains 140 g of a wax with 10.5% phosphorus which still contains a little methanol and sets in a mass in time.

By passing over Amberlite IR 120 H resin (which is an acid resin), the eluent is acid which can indicate the formation of guanidine carboxylate as well as diethylphosphonopropionyl guanidine.

One sets up a bath as in the preceding example, with 2.2% phosphorus, by dissolving 20.5 g of the product obtained in 65 g of water and one brings the pH to 4 by 3,14 g of 85% phosphoric acid. One makes up the bath to volume by 6 g of a totally etherified pentamethylolmelamine, 1.5 g of magnesium chloride hexahydrate, 1.5 g of citric acid and 0.01 g of a wetting agent of the polyethoxylated nonylphenol type and 3 g of a 20% polyethylene emulsion. One pads 30 g of cotton fabric of 280 g/m$^2$ into this bath with a wet pick-up pf 130%.

The fabric then is dried, then placed for ¼ hour in a ventilated drier at 175° C.

The fabric is then washed in water carbonated at 10 g/l at 90° C., for 5 minutes to eliminate the acid residues, then rinsed and tested.

The fabric has a slightly modified hand and shows a slight diminution of its tearing strenght. It has an limit oxygen index greater than 39% which is excellent.

The latter is still greater than 30% after 25 hours of mild washing at 60° C. in the presence of sodium carbonate.

After 25 hours of washing and a rinsing in acidulated water the fabric satisfies the standard DIN 53906 with nil postcombustion and a tear lenght of less than 5cm, which is an index of good fastness to washing.

EXAMPLE 14

One proceeds in the preceding example, but one sets up a bath with only 1.8% of phosphorus in a phosphonic form.

The fabric, after treatment and washing in carbonated water for 5 minutes, has a limit oxygen index of 31.5. This index is still greater than 27% after 18 hours washing at 60° C. in the presence of 3g/l sodium carbonate and 2g/l soap.

EXAMPLE 15

One proceeds as in example 13 but one makes the treated fabric undergo strong washing at 90° C. for 30 minutes in water containing 3g/l sodium carbonate and 2g/l soap.

The limit oxygen index measured according to the standard ASTM D 2863-70 which was 36% at the beginning is 26% after 5 strong washes and the fabric is still flameresistant according to the standard DIN 53906 with a tear lenght less than 7cm and a postcombustion less than 2 seconds.

EXAMPLE 16

One prepares a mole of guanidine in solution in methanol as in example 5.

Into a 1000cc erlenmeyer flask with magnetic agitation and cooled by an ice bath, one puts 141g (0.5 mole) of dimethyldiethylphosphonosuccinate prepared by adding diethyl phosphite to dimethyl fumarate. One pours, during a period of about one hour, the methanolic guanidine solution, whilst keeping the temperature less than 10° C.

One then leaves it for 48 hours under refrigeration, then one concentrates under a vaccuum of 1mm of mercury. One obtains a wax containing 20% methanol and the phosphorus and the nitrogen contents are respectively 7% and 19.6% (theory on a dry product of 9.23 and 25%).

One prepares a bath containing 2.2% phosphorus provided by the product according to the invention by dissolving 31.5g of the product obtained in 30g of water. The pH is controlled to 4.3 by 6.5g of 85% phosphoric acid and one adds 6g of an etherified methylolmelamine, 1.5g of citric acid and 1.5g of hexahydrated magnesium chloride and one makes up the bath to 100.

One pads a cotton fabric into this bath, dries it and one places it for ¼ hour in a ventilated drier at 165° C. The fabric is then washed for 5 minutes at 90° C. in a bath containing 5g/l sodium carbonate, then rinsed and tested.

Its limit oxygen index is greater than 32%. The appearance and feel of the fabric are very little modified and its loss of tearing strenght is slight.

After 26 hours of mild washing at 60° C. in the presence of 3g/l of sodium carbonate and 2g/l of soap and after light acidation, its limit oxygen index is greater than 28%. Tested then according to the standard DIN 53906, it has a tear length of 5.5cm and a nil postcombustion.

EXAMPLE 17

One prepares a crystallised diethylphosphonopropionyl guanidine as in example 14 and one dries it in the drier.

One prepares a bath by dissolving 18g of this product in 40g of water and one adjusts the pH to 5 with phosphoric acid. One makes up to volume with 6g of an etherified methylolmelamine, 1.5g hexahydrated magnesium chloride, 1.5 g citric acid and 0.1 g of an ethoxylated nonyphenol wetting agent.

One makes up the baths' volume to 100 and one pads a cotton fabric of 280g/m$^2$ in it, then dries it. The fabric is heated at 165° C. for ¼ hour then washed for 5 minutes at 90° C. in carbonated water, rinsed and then dried.

Its limit oxygen index is 33.4% and it successfully passes the DIN 53906 test.

After 22 hours washing at 60° C. in a 2g/l soap solution containing 3g/l carbonate of soda and after an acid rinse the limit oxygen index is 28% and the fabric is flame resistant according to the standard DIN 53906.

EXAMPLE 18

Into a 500cc erlenmeyer flask fitted with a magnetic agitator and cooled by an ice bath, one puts 35g (0.16 mole) of ethyl dimethylphosphono-3-propionate. Then one pours, over a period of about 2 hours, 0.5 mole guanidine in solution into the methanol prepared as in example 5, whilst maintaining a temperature lower than 10° C. One keeps it under agitation for 3 further hours, then leaves it for 48 hours under refrigeration.

Then the solution is concentrated under vacuum and one obtains a wax still containing a little methanol and the phosphorus content of which is 7.5%.

One prepares a bath by dissolving 27g of this product in 40g water and one brings the pH to 4 with 85% phosphoric acid one then adds 6g of an etherified methylolmelamine, 2.5g citric acid and 1.5g of hexahydrated magnesium chloride.

One adds 0.1g of a wetting agent of an ethoxylated nonylphenol type and 0.5g of a 20% paraffin in water emulsion.

The fabric is padded, dried then placed for ¼ hour in a ventilated drier regulated at 165° C.

The fabric is then washed in carbonated water at 90° C. for 5 minutes, rinsed then dried.

The limit oxygen index is 48% which is excellent.

After 17 hours of mild washing at 60° C. in a solution containing 2g/l of soap and 3g/l of sodium carbonate and after a slight acidification, its limit oxygen index stabilises at about 34%, which is excellent.

EXAMPLE 19

One proceeds as in example 12 but with 112g of methyl diethylphosphono-propionate. One obtains 150g of a 10.4% phosphorus wax and which still contains a little methanol.

Into a 250cc three necked flask one introduces 128.5g of the above mentioned wax, 16.55g of polyoxymethelene and a small quantity of MgO. One gently raises the temperature to 90° C.; the mass becomes fluid. One adds 39.4g of water. One maintains it at 90° C. for 6 hours. The initial pH of 7-8 tends to drop; one maintains it at about 8 by adding 5g of $Na_2CO_3$. One obtains 185g of a 7% phosphorus solution.

One prepares a bath with 30g of the preceding solution, 15g water, and one adjusts the pH to 3 with 85% phosphorus acid. One adds 8.1g of a 45% solution of totally etherified pentamethylolmelamine, 3.4g of 85% phosphoric acid and one makes it up to volume with water in order to bring it up to 95 g.

One pads a cotton fabric of 230g/m² in the bath, dries it. The weight add on is 14% One raises it to 170° C. for 5 minutes then leaves it to cool.

The fabric is then washed for 5 minutes at 60° C. in a solution of carbonate of soda, then it is dried. Its limit oxygen index is 35%. After 10 hours washing at 60° C. in a soapy carbonate solution the index is still 34%.

This being the case and whatever the method of application adopted one sets out thus a product and a flameproofing process for diverse materials, the characteristics of which follow sufficiently from the above for it to be useless to dwell on this subject and which present, in relation to those which already exist, numerous advantages, especially that of giving to textiles, flame resistance fast to washing and cleaning, without nevertheless altering too much the appearance and the hand of these textiles.

It is self-evident and it follows moreover from the above that the invention is in no way limited to those of its methods of application, nor to those methods of application of its various parts, which have been more especially set out; it takes into account, on the contrary, all the variations.

What we claim is:

1. Phosphonylated amides with a formula:

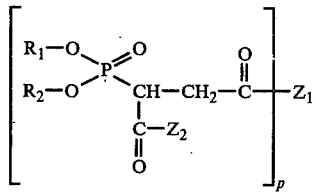

in which:

$R_1$ and $R_2$ represent an alkyl, haloalkyl or alkenyl radical having 1 to 4 atoms of carbon;

$Z_1$ and $Z_2$ represent a residue of a compound containing more than one atom of nitrogen chosen from the group made up of guanidine, alkylguanidines, ethylenediamine, diethylenetriamine, triethylenetetramine, aminoguanidine and hydrazine and its derivatives, and their methylolated or alcoxymethylated derivatives;

$p$ represents the number 1 or 2, except when $Z_1$ is quanidine or an alkylguanidine in which case $p = 1$.

2. Phosphonylated amides with a formula:

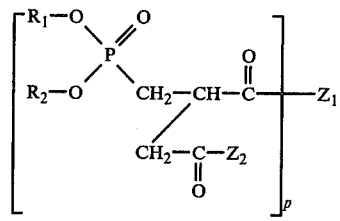

in which:

$R_1$ and $R_3$ represent an alkyl, haloalkyl or alkenyl radical having 1 to 4 atoms of carbon;

$Z_1$ and $Z_2$ represent a residue of a compound containing more than one atom of nitrogen chosen from the group made up of guanidine, alkylguanidines, ethylenediamine, diethylenetriamine, triethylenetetramine, aminoguanidine and hydrazine and its derivatives, and their methylolated or alcoxymethylated derivatives $p$ represents the number 1 or 2, except when $Z_1$ is quanidine or an alkylguanidine in which case $p = 1$.

3. 2-diethylphosphonosuccinyl bis (ethylenediamine).
4. Diethylphosphonosuccinyl-ethylenediamine.
5. 3-diethylphosphonopropionyl-guanidine.
6. 2-diethylphosphonomethylene-succinyl-bis (guanidine).
7. 3-diethylphosphono-2-methyl-propionyl-guanidine.
8. 3-diethylphosphono-3-methyl-propionyl-guanidine.
9. 3-diethylphosphonopropionyl-ethylenediamine.
10. 3-diethylphosphonopropionyl-hydrazine.
11. 3-dimethylphosphonopropionyl-guanidine.
12. 2-diethylphosphono-succinyl bis(guanidine).

* * * * *